United States Patent
An et al.

(10) Patent No.: US 11,173,310 B2
(45) Date of Patent: Nov. 16, 2021

(54) MULTI-SENSOR BASED CARDIAC STIMULATION

(71) Applicant: Cardiac Pacemakers, Inc., St. Paul, MN (US)

(72) Inventors: Qi An, Blaine, MN (US); Julie A. Thompson, Circle Pines, MN (US); Yinghong Yu, Shoreview, MN (US); Yi Zhang, Plymouth, MN (US); Pramodsingh Hirasingh Thakur, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 195 days.

(21) Appl. No.: 16/427,044

(22) Filed: May 30, 2019

(65) Prior Publication Data

US 2019/0275338 A1   Sep. 12, 2019

Related U.S. Application Data

(63) Continuation of application No. 15/334,615, filed on Oct. 26, 2016, now Pat. No. 10,350,418.

(Continued)

(51) Int. Cl.
*A61N 1/365* (2006.01)
*A61N 1/368* (2006.01)
(Continued)

(52) U.S. Cl.
CPC ....... *A61N 1/36585* (2013.01); *A61N 1/3627* (2013.01); *A61N 1/3682* (2013.01);
(Continued)

(58) Field of Classification Search
CPC ............ A61N 1/36585; A61N 1/36842; A61N 1/36843; A61N 1/3627; A61N 1/36514;
(Continued)

(56) References Cited

U.S. PATENT DOCUMENTS

| 8,301,250 B2 | 10/2012 | Rom |
| 8,731,667 B2 | 5/2014 | Maskara et al. |
| (Continued) | | |

FOREIGN PATENT DOCUMENTS

| CN | 102481453 A | 5/2012 |
| CN | 104244809 A | 12/2014 |
| (Continued) | | |

OTHER PUBLICATIONS

"U.S. Appl. No. 15/334,615, Notice of Allowance dated Mar. 6, 2019", 9 pgs.

(Continued)

*Primary Examiner* — Erin M Piateski
(74) *Attorney, Agent, or Firm* — Schwegman Lundberg & Woessner, P.A.

(57) ABSTRACT

Devices and methods for improving device therapy such as cardiac resynchronization therapy by determining a value for a device parameter are described. An ambulatory medical device (AMD) can include a sensor circuit to sense a physiological signal and generate two or more signal metrics, and detect an event of worsening cardiac condition using the two or more signal metrics. In response to the detection of worsening cardiac condition, the AMD can determine, for a stimulator, a value of at least one stimulation parameter based on temporal responses of two or more signal metrics. The temporal responses include near-term and long-term responses to the stimulation. The AMD can program the stimulator with the determined parameter value, and generate stimulation according to the determined parameter value to stimulate target tissue.

20 Claims, 8 Drawing Sheets

Related U.S. Application Data

(60) Provisional application No. 62/246,293, filed on Oct. 26, 2015.

(51) Int. Cl.
*A61N 1/372* (2006.01)
*A61N 1/362* (2006.01)
*A61B 7/04* (2006.01)

(52) U.S. Cl.
CPC ..... *A61N 1/36514* (2013.01); *A61N 1/36842* (2017.08); *A61N 1/36843* (2017.08); *A61N 1/37264* (2013.01); *A61B 7/04* (2013.01); *A61N 1/3655* (2013.01); *A61N 1/3684* (2013.01); *A61N 1/36521* (2013.01); *A61N 1/36535* (2013.01); *A61N 1/36564* (2013.01); *A61N 1/36592* (2013.01)

(58) Field of Classification Search
CPC .............. A61N 1/3682; A61N 1/37264; A61N 1/36521; A61N 1/36535; A61N 1/3655; A61N 1/36564; A61N 1/36592; A61N 1/3684; A61B 7/04
USPC .......................................................... 607/18
See application file for complete search history.

(56) References Cited

U.S. PATENT DOCUMENTS

| | | | |
|---|---|---|---|
| 10,350,418 B2 | 7/2019 | An et al. | |
| 2005/0080460 A1 | 4/2005 | Wang et al. | |
| 2005/0115561 A1 | 6/2005 | Stahmann | |
| 2005/0234517 A1 | 10/2005 | Braunschweig et al. | |
| 2006/0282000 A1 | 12/2006 | Zhang et al. | |
| 2007/0260285 A1 | 11/2007 | Libbus et al. | |
| 2009/0299211 A1* | 12/2009 | Wenzel ................ | A61B 5/7282 600/547 |
| 2011/0015704 A1* | 1/2011 | Ternes ................... | A61B 5/363 607/62 |
| 2013/0116578 A1 | 5/2013 | An et al. | |
| 2015/0094784 A1 | 4/2015 | Karst et al. | |
| 2015/0157221 A1 | 6/2015 | An et al. | |
| 2016/0045754 A1* | 2/2016 | Libbus ................ | A61N 1/36053 607/5 |
| 2017/0113052 A1 | 4/2017 | An et al. | |

FOREIGN PATENT DOCUMENTS

| | | |
|---|---|---|
| CN | 108348751 A | 7/2018 |
| WO | WO-2011008749 A2 | 1/2011 |
| WO | WO-2017074999 A1 | 5/2017 |

OTHER PUBLICATIONS

"U.S. Appl. No. 15/334,615, Restriction Requirement dated Mar. 29, 18", 9 pgs.

"European Application Serial No. 16790851.6, Response filed Dec. 17, 18 to Communication Pursuant to Rules 161 and 162 dated Jun. 8, 2018", 23 pgs.

"International Application Serial No. PCT/US2016/058776, International Preliminary Report on Patentability dated May 11, 2018", 8 pgs.

"International Application Serial No. PCT/US2016/058776, International Search Report dated Feb. 13, 2017", 5 pgs.

"International Application Serial No. PCT/US2016/058776, Written Opinion dated Feb. 13, 2017", 6 pgs.

Tassin, Aude, et al., "Relationship between Amplitude and Timing of Heart Sounds and Endocardial Acceleration", Pacing and Clinical Electrophysiology, vol. 32, Issue Supplement s1, pp. S101-S104, Mar. 2009.

Waggoner, A. D, et al., "Improvements in left ventricular diastolic function after cardiac resynchronization therapy are coupled to response in systolic performance", J Am Coll Cardiol., 46(12), (Dec. 20, 2005), 2244-9.

"Chinese Application Serial No. 201680062553.7, Office Action dated Dec. 25, 2020", w/English translation, 33 pgs.

* cited by examiner

MULTI-SENSOR BASED CARDIAC STIMULATION

CLAIM OF PRIORITY

This application is a continuation of U.S. application Ser. No. 15/334,615, filed Oct. 26, 2016, which claims the benefit of priority under 35 U.S.C. § 119(e) of U.S. Provisional Patent Application Ser. No. 62/246,293, filed on Oct. 26, 2015, each of which is herein incorporated by reference in its entirety.

TECHNICAL FIELD

This document relates generally to medical devices, and more particularly, to systems, devices and methods for improving a device therapy using multiple sensors.

BACKGROUND

Congestive heart failure (CHF) is a major health problem and affects many people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction are delayed, and the left and right ventricles do not contract simultaneously. Non-simultaneous contractions of the left and right ventricles further decrease the pumping efficiency of the heart.

Overview

CHF can be treated by cardiac pacing therapy. Pacing therapy to promote synchronization of heart chamber contractions for improved cardiac function is generally referred to as cardiac resynchronization therapy (CRT). Ambulatory medical devices such as cardiac pacemakers are capable of delivering CRT by pacing multiple heart chambers. Some ambulatory medical devices can pace the heart chambers in a sequence that causes the heart chambers to contract in synchrony, thereby increasing the pumping power of the heart and delivering more blood to the peripheral tissues of the body. In the case of dyssynchrony of right and left ventricular contractions, a biventricular pacing therapy can be used to resynchronize the left and right ventricles. Bi-atrial pacing or pacing of all four heart chambers can also be used.

Improving the CRT therapy by determining desired CRT parameters involves determining desired pacing parameters, such as intervals between pacing pulses delivered to various heart chambers. In addition to cross-patient differences in their responses to CRT, within-patient variation in optimal CRT setting may also exist such as due to changes in the patient's activity level, disease progression, medication, and general health condition. As a result, to achieve therapeutic effect of CRT such as improved cardiac hemodynamics, device parameters may be timely adjusted on an individualized basis.

Physiological sensors can be used to detect a patient's response to the CRT therapy, which provides information for optimizing the CRT therapy. However, the physiologic sensors, or signal metrics derived from the sensor signals, may demonstrate different signal characteristics during and following the stimulation. The present inventors have recognized that some physiological sensors or signal metrics can be more responsive to stimulation than some other sensors or signal metrics. The present inventors have also recognized that some sensors or signal metrics may demonstrate different temporal responses to stimulation. A sensor or signal metric's reliability for detecting patient responses, such as hemodynamic status, may vary with time. At least with these issues in consideration, the present inventors have recognized that there remains a considerable need for improving device therapy using multiple sensors.

Various examples described herein can improve device therapy such as cardiac resynchronization therapy (CRT). In an example, an ambulatory medical device (AMD) can include a sensor circuit to sense a physiological signal and generate two or more signal metrics, and detect an event of worsening cardiac condition using the two or more signal metrics. In response to the detection of worsening cardiac condition, the AMD can determine, for a stimulator, a desired value of at least one stimulation parameter based on temporal responses of two or more signal metrics such as during or after the stimulation. The temporal responses can include near-term and long-term responses to the stimulation. The AMD can program the stimulator with the determined parameter value, and generate stimulation according to the determined parameter value to stimulate target tissue.

In Example 1, an ambulatory medical device (AMD) can comprise a stimulation generator circuit, a signal sensor circuit, a cardiac condition detector circuit, and a stimulation programmer circuit. The stimulation generator circuit can generate stimulation for stimulating a target tissue in a patient according to at least one stimulation parameter. The signal sensor circuit can include a sense amplifier circuit to sense one or more physiological signals and a filter circuit to generate two or more signal metrics from the sensed one or more physiological signals. The cardiac condition detector circuit can include a blending circuit that uses the two or more signal metrics to generate a cardiac condition indicator, and a comparator circuit that detects an event of worsening cardiac condition using the cardiac condition indicator. The stimulation programmer circuit can be coupled to the cardiac condition detector circuit and the signal sensor circuit. In response to the detection of the event of worsening cardiac condition, the stimulation programmer circuit can determine a parameter value for the stimulation parameter based on information about temporal responses of the two or more signal metrics. The stimulation programmer circuit can program the stimulation generator circuit with the determined parameter value.

Example 2 can include, or can optionally be combined with the subject matter of Example 1 to optionally include, the cardiac condition detector circuit that can generate a hemodynamic status indicator using two or more signal metrics from one or more of a heart sound signal, an impedance signal, a blood pressure signal, a respiration signal, or a cardiac timing interval signal, the hemodynamic status indicator indicating a change or a rate of change of hemodynamic status of the patient. The stimulation programmer circuit can determine the parameter value when the hemodynamic status indicator falls outside a specified range.

Example 3 can include, or can optionally be combined with the subject matter of one or any combination of Examples 1 or 2 to include, the cardiac condition detector circuit that can generate a metabolic demand indicator using one or more of a heart rate signal, a respiration signal, a posture signal, a time signal, a temperature signal, a perspiration signal, or a physical activity signal, the metabolic demand indicator indicating a change of metabolic demand in the patient. The stimulation programmer circuit can determine the parameter value when the metabolic demand indicator falls outside a specified range.

Example 4 can include, or can optionally be combined with the subject matter of one or any combination of Examples 1 through 3 to include, the cardiac condition detector circuit that can receive information about development of comorbidity in heart failure (HF), which can include presence or severity of one or more of hypertension, atrial fibrillation, diabetes mellitus, pneumonia, or renal failure. The stimulation programmer circuit can determine the parameter value in response to the development of comorbidity in HF.

Example 5 can include, or can optionally be combined with the subject matter of one or any combination of Examples 1 through 4 to include, a timer circuit to determine time elapsed during which the at least one stimulation parameter is set and maintained at a specified parameter value. The stimulation programmer circuit can determine the parameter value in response to the elapsed time exceeds a specified threshold.

Example 6 can include, or can optionally be combined with the subject matter of one or any combination of Examples 1 through 5 to include, the stimulation generator circuit that can generate cardiac stimulation at one or more targets sites in a heart according to at least one stimulation parameter.

Example 7 can include, or can optionally be combined with the subject matter of Example 6 to optionally include, the stimulation generator circuit that can generate cardiac resynchronization therapy (CRT) stimulation of a first site of a left ventricle (LV) of the heart and a second site of a right ventricle (RV) of the heart, according to one or more stimulation parameters including an atrio-ventricular delay (AVD), a RV-LV delay (VVD), or a lower rate limit (LRL) for stimulation.

Example 8 can include, or can optionally be combined with the subject matter of Example 6 to optionally include, the stimulation generator circuit that can generate multisite stimulation of at least first and second sites of a left ventricle (LV), according to one or more stimulation parameters including an atrio-ventricular delay (AVD) or a relative timing between the stimulation of at least the first and second sites of the LV.

Example 9 can include, or can optionally be combined with the subject matter of one or any combination of Examples 1 through 8 to include, the stimulation programmer circuit that can include a sensor dynamic response analyzer circuit, a weight factor generator circuit, and a blending circuit. The sensor dynamic response analyzer circuit can determine respective dynamic response indicators based on the information about the temporal responses of the two or more signal metrics. The dynamic response indicators can indicate responsiveness of the two or more signal metrics to the stimulation. The weight factor generator circuit can produce, for the two or more signal metrics, respective weight factors using the respective dynamic response indicators. The blending circuit can generate a stimulation efficacy indicator using a combination of at least some of the two or more signal metrics each weighted by the respective weight factor. The stimulation programmer circuit can determine the parameter value for the at least one stimulation parameter when the stimulation efficacy indicator meets a specified condition.

Example 10 can include, or can optionally be combined with the subject matter of Example 9 to optionally include, the sensor dynamic response analyzer circuit that an determine, for the two or more signal metrics, respective dynamic response indicators including one or more of near-term response indicators during a near-term period ($T_N$) with reference to the stimulation, or one or more long-term response indicators during a long-term period ($T_L$) with reference to the stimulation. The weight factor generator circuit can produce, for the two or more signal metrics, respective weight factors including one or more of near-term weight factors ($W_N$) corresponding to the near-term period or long-term weight factors ($W_L$) corresponding to the long-term period. The blending circuit can generate the stimulation efficacy indicator including a near-term stimulation efficacy indicator using a combination of at least some of the two or more signal metrics each weighted by the respective near-term weight factors, or a long-term stimulation efficacy indicator using a combination of at least some of the two or more signal metrics each weighted by the respective long-term weight factors.

Example 11 can include, or can optionally be combined with the subject matter of Example 10 to optionally include, the weight factor generator circuit that can produce, for the two or more signal metrics, respective weight functions describing weight factor as a respective function of time.

Example 12 can include, or can optionally be combined with the subject matter of Example 11 to optionally include, the weight factor generator circuit that can generate a decay weight function of time if the corresponding signal metric is more responsive to stimulation during the near-term period than during the long-term period.

Example 13 can include, or can optionally be combined with the subject matter of Example 11 to optionally include, the weight factor generator circuit that can generate growth weight function of time if the corresponding signal metric is less responsive to stimulation during the near-term period than during the long-term period.

Example 14 can include, or can optionally be combined with the subject matter of Example 9 to optionally include, a sensor metric selector circuit to receive information about selection or deselection among the two or more signal metrics according to the at least one stimulation parameter. The blending circuit can generate the stimulation efficacy indicator using a combination of the selected signal metrics each weighted by the respective weight factor.

Example 15 can include, or can optionally be combined with the subject matter of Example 14 to optionally include, the stimulation generator circuit that can deliver cardiac resynchronization therapy (CRT) stimulation to a right ventricle (RV) and a left ventricle (LV) of the heart. The sensor metric selector circuit can receive information including a selection of one or more of S1 amplitude or heart rate if the stimulation parameter is atrio-ventricular delay (AVD), a selection of at least Q-LV interval if the stimulation parameter is RV-LV delay (VVD), a selection of at least a blood pressure metric if the stimulation parameter is lower rate limit LRL, or a selection of one or more of impedance metric or physical activity metric if the stimulation parameter is capture threshold.

In Example 16, an ambulatory medical device (AMD) can comprise a stimulation generator circuit, a signal sensor circuit, a cardiac condition detector circuit, and a stimulation programmer circuit. The stimulation generator circuit can generate stimulation for stimulating a target tissue in a patient according to at least one stimulation parameter. The signal sensor circuit can include a sense amplifier circuit to sense one or more physiological signals and a filter circuit to generate two or more signal metrics from the sensed one or more physiological signals. The cardiac condition detector circuit can include a blending circuit that uses the two or more signal metrics to generate a cardiac condition indicator, and a comparator circuit that detects an event of worsening cardiac condition using the cardiac condition indicator. The stimulation programmer circuit can be coupled to the cardiac condition detector circuit and the signal sensor circuit. In response to the detection of the event of worsening cardiac condition, the stimulation programmer circuit can adjust at least one stimulation parameter and program the stimulation generator circuit to deliver stimulation using the adjusted at least one stimulation parameter. The stimulation programmer circuit can determine an effectiveness of the adjustment or whether further adjustment of the at least one stimulation parameter is needed based on information about temporal responses of the two or more signal metrics.

In Example 17, a method can include steps of sensing one or more physiological signals and generating two or more signal metrics from the sensed one or more physiological signals, generating a cardiac condition indicator using the two or more signal metrics, and detecting an event of worsening cardiac condition using the cardiac condition indicator. The method can include, in response to the detection of the event of worsening cardiac condition, configuring a stimulator by adjusting a parameter value of at least one stimulation parameter and generating stimulation according to the at least one stimulation parameter with the adjusted parameter value, and delivering the stimulation to a target tissue in a patient. The method can include sensing temporal responses of the two or more signal metrics during or after the stimulation, the temporal responses each including near-term and long-term responses to the stimulation. The method can include determining a parameter value for the at least one stimulation parameter using the temporal responses, and programming the stimulation generator with the determined parameter value.

Example 18 can include, or can optionally be combined with the subject matter of Example 17 to optionally include, the step of generating a cardiac condition indicator, which can include one or more of: generating a hemodynamic status indicator using two or more signal metrics from one or more of a heart sound signal, an impedance signal, a blood pressure signal, a respiration signal, or a cardiac timing interval signal, the hemodynamic status indicator indicating a change or a rate of change of hemodynamic status of the patient; generating a metabolic demand indicator using one or more of a heart rate signal, a respiration signal, a posture signal, a time signal, a temperature signal, a perspiration signal, or a physical activity signal, the metabolic demand indicator indicating a change of metabolic demand in the patient; or receiving information about development of comorbidity in heart failure (HF) including presence or severity of one or more of hypertension, atrial fibrillation, diabetes mellitus, pneumonia, or renal failure. The parameter value can be determined in response to the hemodynamic status indicator or the metabolic demand indicator falling outside a respective range, or the development of comorbidity in HF.

Example 19 can include, or can optionally be combined with the subject matter of Example 17 to optionally include, timing elapsed time during which the at least one stimulation parameter is set and maintained at a specified parameter value. The parameter value can be determined in response to the elapsed time exceeds a specified threshold.

Example 20 can include, or can optionally be combined with the subject matter of Example 17 to optionally include, generating the stimulation including cardiac resynchronization therapy (CRT) stimulation of a first site of a left ventricle (LV) of the heart and a second site of a right ventricle (RV) of the heart, according to one or more stimulation parameters including an atrio-ventricular delay (AVD), a RV-LV delay (VVD), or a lower rate limit (LRL) for stimulation.

Example 21 can include, or can optionally be combined with the subject matter of Example 17 to optionally include, generating the stimulation including multisite stimulation of at least first and second sites of a left ventricle (LV), according to one or more stimulation parameters including an atrio-ventricular delay (AVD) or a relative timing between the stimulation of at least the first and second sites of the LV.

Example 22 can include, or can optionally be combined with the subject matter of Example 17 to optionally include, determining the parameter value for the at least one stimulation parameter which can include one or more steps of: based on the information about the temporal responses of the two or more signal metrics, determining respective dynamic response indicators indicating responsiveness of the two or more signal metrics to the stimulation; producing, for the two or more signal metrics, respective weight factors using the respective dynamic response indicators; generating a stimulation efficacy indicator using a combination of at least some of the two or more signal metrics each weighted by the respective weight factor; and determining the parameter value for the at least one stimulation parameter when the stimulation efficacy indicator meets a specified condition.

Example 23 can include, or can optionally be combined with the subject matter of Example 22 to optionally include, producing the dynamic response indicators which can include one or more of near-term response indicators during a near-term period (TN) with reference to the stimulation, or one or more long-term response indicators during a long-term period (TL) with reference to the stimulation. The weight factors can include, for the two or more signal metrics, respective one or more of near-term weight factors (WN) corresponding to the near-term period or long-term weight factors (WL) corresponding to the long-term period. The stimulation efficacy indicator can include a near-term stimulation efficacy indicator or a long-term stimulation efficacy indicator. The near-term stimulation efficacy indicator can be generated using a combination of at least some of the two or more signal metrics each weighted by the respective near-term weight factors. The long-term stimulation efficacy indicator can be generated using a combination of at least some of the two or more signal metrics each weighted by the respective long-term weight factors.

Example 24 can include, or can optionally be combined with the subject matter of Example 23 to optionally include, producing the respective weight factors which includes weight functions describing weight factor as a respective function of time. The weight function can include a decay function of time if the corresponding signal metric is more responsive to stimulation during the near-term period than during the long-term period, or a growth function of time if the corresponding signal metric is less responsive to stimulation during the near-term period than during the long-term period.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices and methods for improving a device therapy using multiple sensor metrics. The device therapy can include cardiac pacing therapy provided by an implantable medical device such as a pacemaker, an implantable cardioverter-defibrillator (ICD), or cardiac resynchronization therapy (CRT) device. The improvement of the cardiac pacing therapy can include determining a value for a relative timing between a first event in a heart chamber and a second event in a different heart chamber, such as intervals between pacing pulses delivered to atria and ventricles that provide effective CRT delivery. The present document discussed methods and devices for improving the device parameters using multiple sensor metrics and information fusion. The methods and devices described herein can also be applicable to improving other device functions pertaining to an implantable medical device, including such as pacing therapy, defibrillation therapy, neural stimulation therapy, and patient diagnostics and stratifying a patient's risk of developing a disease or a condition, or to monitoring a patient's health status or response to a medical intervention.

Figure 1:
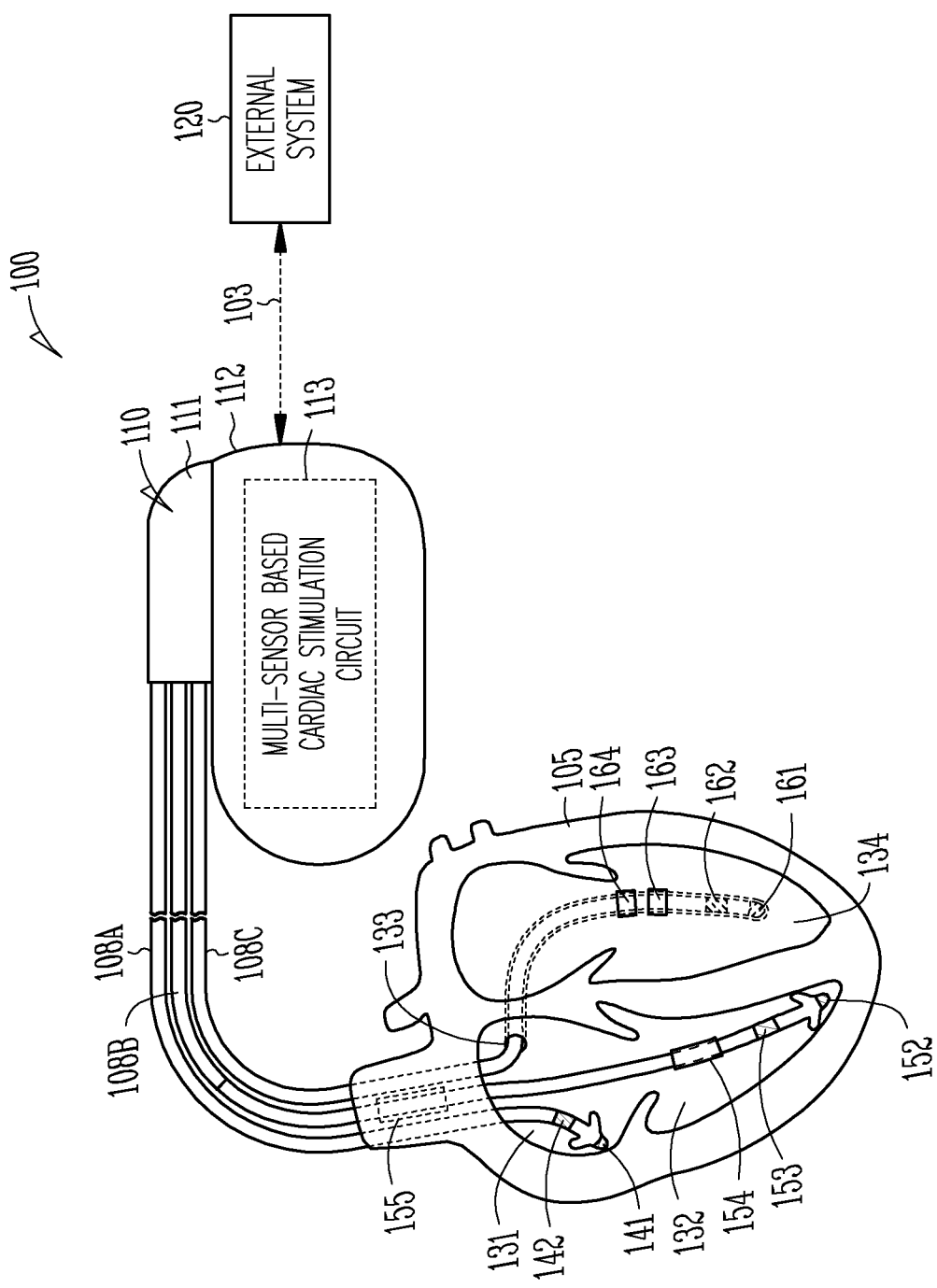
FIG. 1 illustrates generally an example of cardiac rhythm management (CRM) system and portions of the environment in which the CRM system operates.

FIG. 1 illustrates generally an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). It is also contemplated that, in other examples, the IMD 110 can include one or more monitoring or therapeutic devices such as a subcutaneously implanted device, a neural stimulator, a drug delivery device, a biological therapy device, a diagnostic device, or one or more other ambulatory medical devices. The IMD 110 may be coupled to, or may be substituted by a monitoring medical device such as a bedside or other external monitor. It is further contemplated that the device may not be an implantable device, but instead may be an external device. For example, the ambulatory medical device can include an external monitoring or therapeutic devices such as, for example, a wearable monitoring device or a wearable cardioverter defibrillator.

As illustrated in FIG. 1, the IMD 110 can include a hermetically sealed can housing 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and allow delivery of one or more resynchronization pacing pulses from the LV. Additional electrodes can be included in or along the lead 108C. In an example, as illustrated in FIG. 1, a third electrode 163 and a fourth electrode 164 can be included in the lead 108. In some examples (not shown in FIG. 1), at least one of the leads 108A-C, or an additional lead other than the leads 108A-C, can be implanted under the skin surface without being within at least one heart chamber, or at or close to heart tissue.

The IMD 110 can include an electronic circuit that can sense a physiological signal. The physiological signal can include an electrogram or a signal representing mechanical function of the heart 105. The hermetically sealed can housing 112 may function as an electrode such as for sensing or pulse delivery. For example, an electrode from one or more of the leads 108A-C may be used together with the can housing 112 such as for unipolar sensing of an electrogram or for delivering one or more pacing pulses. A defibrillation electrode from the lead 108B may be used together with the can housing 112 such as for delivering one or more cardioversion/defibrillation pulses. In an example, the IMD 110 can sense impedance such as between electrodes located on one or more of the leads 108A-C or the can housing 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiological signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of thoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are contemplated.

As illustrated, the CRM system 100 can include a multi-sensor based cardiac stimulation circuit 113, which can detect an event triggering a process of determining a value of a device parameter, such as a parameter associated with a device therapy, diagnostic information, physiological event sensing, or device operation and functionality. Examples of the triggering event can include an event indicative of worsening heart failure (HF) or other cardiac conditions, which can be detected using one or more physiological signals sensed by one or more electrodes located on one or more of the leads 108A-C or the can 112, or other physiologic sensors. Once a triggering event is detected, the cardiac stimulation circuit 113 can determine a value of a device parameter, such as a stimulation parameter that controls the timing of the stimulation pulses delivered at the heart. One example of the stimulation parameter includes an atrial-ventricular delay (AVD) between an intrinsically occurred atrial electrical activation signal (As) such as sensed by the electrodes on the lead 108A and a subsequent ventricular pacing pulse (Vp) such as delivered through the electrodes on the lead 108B, or between an atrial pacing pulse (Ap) such as delivered through the electrodes on lead 108A and the subsequent Vp. Another example of the stimulation parameter includes a left ventricular-right ventricular delay (VVD), latency between a left ventricular pacing pulse (LVp) such as delivered through the electrodes on the lead 108C and a right ventricular pacing pulse (RVp) such as delivered through the electrodes on the lead 108B. In determining a value for a device parameter, the multi-sensor based cardiac stimulation circuit 113 can be coupled to one or more physiologic sensors or sensing electrodes such as the electrodes on one or more of the leads 108A-C and receive physiological signals from the physiologic sensors or electrodes. The IMD 110 can program the stimulations (such as atrial pacing pulses, ventricular pacing pulses, cardioversion pulses, defibrillation pulses, or neural stimulations) and schedule the delivering of the stimulations using the determined device parameter value. Examples of the multi-sensor based cardiac stimulation circuit 113 are discussed below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The worsening cardiac condition detector 113 may be implemented in the external system 120. The external system 120 can be configured to detect an event of worsening cardiac condition using data extracted from the IMD 110 or data stored in a memory within the external system 120. Portions of the worsening cardiac condition detector 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
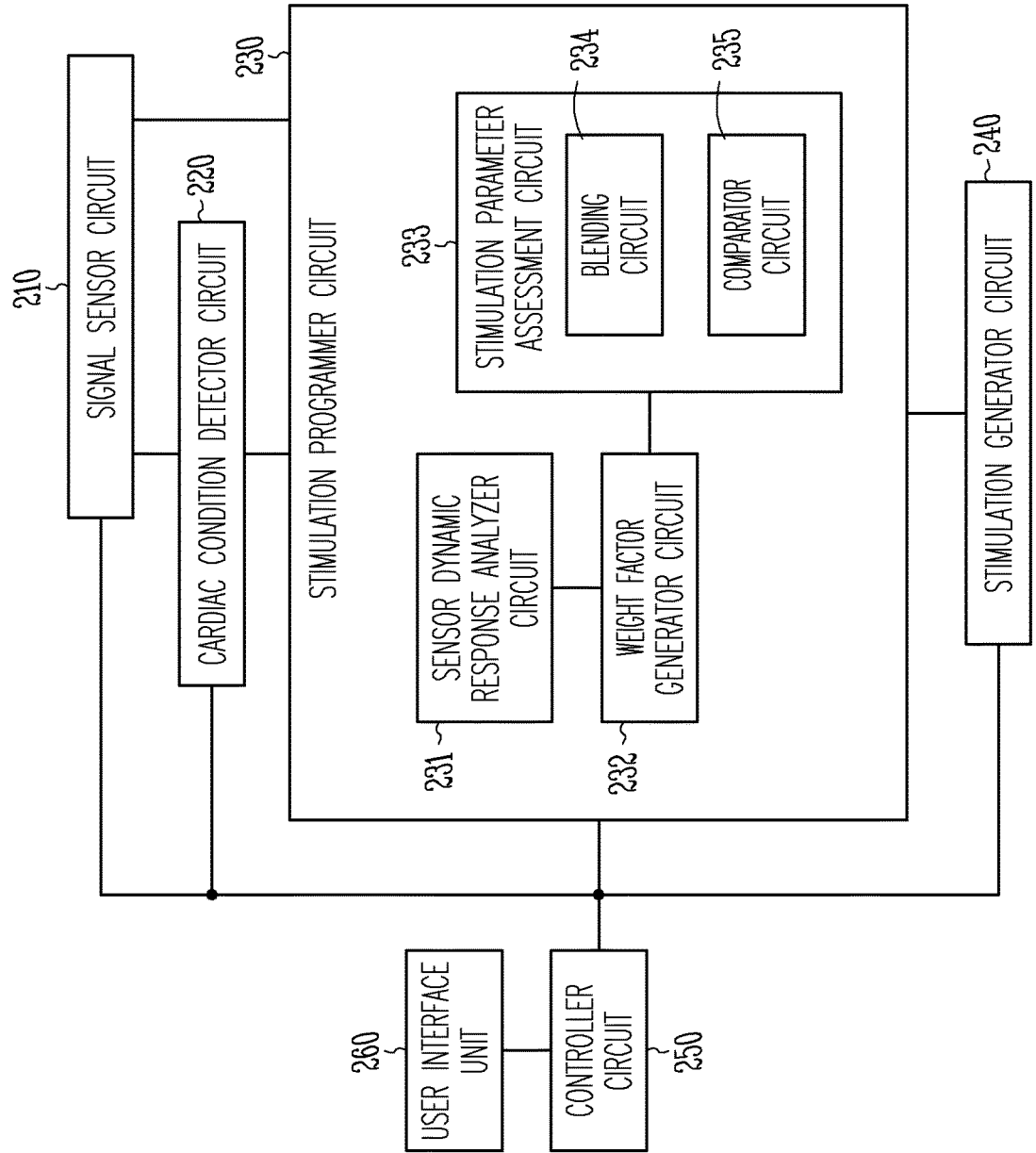
FIG. 2 illustrates generally an example of a device therapy adjustment circuit.

FIG. 2 illustrates generally an example of a device therapy adjustment circuit 200, which can be an example of the multi-sensor based cardiac stimulation circuit 113. The device therapy adjustment circuit 200 can include subcircuits including a signal sensor circuit 210, a cardiac condition detector circuit 220, a stimulation programmer circuit 230, a stimulation generator circuit 240, a controller circuit 250, and a user interface unit 260. The subcircuits of the device therapy adjustment circuit 200 can be implemented within an implantable or a wearable medical device, or distributed between two or more implantable or wearable medical devices. In an example, the HF risk detector circuit 220 can be implemented in a diagnostic medical device, and the stimulation programmer circuit 230 and the stimulation generation circuit 240 can be implemented in a therapeutic medical device.

The signal sensor circuit 210 can include a sense amplifier circuit to sense one or more physiological signals. Examples of the physiological signal can include electrocardiograph (ECG), an electrogram (EGM), an intrathoracic impedance signal, an intracardiac impedance signal, an arterial pressure signal, a pulmonary artery pressure signal, a RV pressure signal, a LV coronary pressure signal, a coronary blood temperature signal, a blood oxygen saturation signal, a heart sound (HS) signal, a posture signal, a physical activity signal, or a respiration signal including. In an example, the signal sensor circuit 210 can be couple to one or more electrodes such as on one or more of the leads 108A-C and the can 112 connected to the IMD 110, or to couple to one or more implantable, wearable, or other ambulatory physiologic sensors to sense one or more physiological signals. Examples of physiologic sensors can include pressure sensors, flow sensors, impedance sensors, accelerometers, microphone sensors, respiration sensors, temperature sensors, or blood chemical sensors, among others. In an example, the signal sensor circuit 210 can be coupled to a device capable of collecting or storing the physiologic information, such as an external programmer, an electronic medical record (EMR) system, or a memory unit, among other data storage devices.

The sense amplifier circuit can pre-process the one or more physiological signals, including, for example, amplification, digitization, filtering, or other signal conditioning operations. The signal sensor circuit 210 can generate two or more signal metrics from the preprocessed one or more physiological signals. The signal metrics can represent a physiologic change in response to patient's disease progression, change in medication, change in health conditions, or change in posture or activity levels. In an example, the signal sensor circuit 210 can receive a transthoracic impedance signal from the electrodes on one or more of the implantable leads such as 108A-C and the can 112, and generate a signal metric of direct-current (DC) impedance using the transthoracic impedance signal. In another example, the signal sensor circuit 210 can receive a HS signal from an accelerometer or an acoustic sensor coupled to the IMD 110, and generate two or more HS metrics. Examples of the HS metrics can include intensities of S1, S2, S3, or S4 heart sounds, or timing of the S1, S2, S3, or S4 heart sound with respect to a fiducial point such as a P wave, Q wave, or R wave in an ECG. In an example, the signal sensor circuit 210 can receive multiple physiological signals from multiple sensors. For example, the signal sensor circuit 210 can receive a blood pressure signal from a pressure sensor and generate two or more blood pressure signal metrics which can include systolic blood pressure, diastolic blood pressure, mean arterial pressure, and the timing metrics of these pressure measurements with respect to a fiducial point.

The cardiac condition detector circuit 220 can use the sensed physiological signals from the signal sensor circuit 210 to detect an event indicative of worsening cardiac condition, such as an event of worsening HF. In an example, the cardiac condition detector circuit 220 can measure a change, or a rate of change, of one or more signal metrics, and detect the worsening cardiac condition if the change or the rate of change of the signal metric meets a specified criterion. In some examples, the cardiac condition detector circuit 220 can detect the worsening cardiac condition using a combination of changes or rate of changes of multiple signal metrics. The detection of the worsening cardiac condition can be used to trigger a process for adjustment of a device parameter and determination of a value for the device parameter, such as a parameter that controls the timing of electrical stimulation therapy at a target site. Other information, such as progression of an existing disease or development of a new disease, can also be used to trigger the device parameter adjustment process. Examples of the cardiac condition detector circuit 220 are discussed below, such as with reference to FIG. 3.

The stimulation programmer circuit 230, coupled to the signal sensor circuit 210 and the cardiac condition detector circuit 220, can be configured to determine a value of a stimulation parameter upon the detection of a triggering event, and program the stimulation generator circuit 240 with the determined parameter value. Determination of the parameter value can be based on information about temporal responses of the two or more signal metrics, such as during or after the stimulation. The temporal responses can include near-term and long-term responses to the stimulation. Examples of the stimulation parameter can include an atrial-ventricular delay (AVD), a left ventricular-right ventricular delay (VVD), or a lower rate limit (LRL), among other parameters controlling the timing of delivering electrical stimulation to one or more sites of the heart. The AVD represents the latency between an intrinsically occurred atrial electrical activation signal (As) and a subsequent ventricular pacing pulse (Vp), or between an atrial pacing pulse (Ap) and the subsequent Vp. The VVD represents the latency between a left ventricular pacing pulse (LVp) and a right ventricular pacing pulse (RVp). The LRL indicates a lowest rate that a cardiac stimulation may be initiated. In some examples, the stimulation programmer circuit 230 can additionally or alternatively determine other device parameters such as used for sensing a physiologic event, providing patient diagnostic information, or assessing device operation and functionality.

The stimulation programmer circuit 230 can be implemented as a part of a microprocessor circuit in the CRM system 100, such as within the IMD 110 or within the external system 120, or distributed between the IMD 110 and the external system 120. The microprocessor circuit can be a dedicated processor such as a digital signal processor, application specific integrated circuit (ASIC), microprocessor, or other type of processor for processing information including heart sounds. Alternatively, the microprocessor circuit can be a general purpose processor that can receive and execute a set of instructions of performing the functions, methods, or techniques described herein.

In an example such as illustrated in FIG. 2, the stimulation programmer circuit 230 can include circuit sets comprising one or more other circuits or subcircuits, including a sensor dynamic response analyzer circuit 231, a weight factor generator circuit 232, and a stimulation parameter assessment circuit 233. The circuit sets may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Upon the detection of a triggering event, such as an event of worsening HF produced by the cardiac condition detector circuit 220, the circuit sets in the stimulation programmer circuit 230 can adjust the value of one or more stimulation parameters (e.g., AVD, VVD, or LRL, among others), assess two or more signal metrics obtained during or after stimulation according to the stimulation parameter programmed to the adjusted parameter value, and determine the value for the stimulation parameter. The adjustment of the parameter value can be automatically performed such as by sweeping through a plurality of candidate parameter values stored in a memory circuit, or by starting with an initial candidate parameter value and then incrementally increasing or decreasing the parameter value by a specified step size. Alternatively, the user interface unit 260 can accept at least partially manual input of candidate parameter values by a system user. The stimulation generator circuit 240 can generate electrical stimulation according to the stimulation parameter with the adjusted parameter value, and deliver the stimulation to the target tissue, such as one or more sites of the heart.

During or after the stimulation, the signal sensor circuit 210 can sense one or more physiological signals and generate two or more signal metrics using the sensed physiological signals. These signals or signal metrics, which are used to determine the parameter value, can be sensed by one or more sensors coupled to the cardiac condition detector circuit 220 that sense the physiological signals used for detecting the worsening cardiac condition, such as worsening HF. Examples of the signal metrics obtained from the physiological signals sensed during or after the stimulation can include: intensities (such as amplitudes) and timing of P wave, Q wave, R wave, QRS complex, or T wave detected from a ECG signal; timing of sensed activation of at least a portion of a chamber of the heart such as RA, RV, LA, and LV, obtained from the intracardiac EGMs; electrical delay of a chamber of the heart such as LV electrical delay; interventricular conduction delay measured as the delay between LV activation to RV activation (LV-RV) delay; intraventricular delay; intensity of a component of the sensed HS signal including one or more of S1, S2, S3, or S4 heart sounds; mechanical delay such as time intervals indicative of systole or diastole; pressures inside a heart chamber; end-systolic volume; or end-diastolic volume; among others.

The signal metrics can be predictive of patient hemodynamic response to the therapeutic cardiac electrostimulation. For example, the electrical delay can include a Q-LV interval measured from Q wave to left ventricle activation, measured from the onset of the intrinsic QRS (such as from the surface ECG) to local intrinsic activation at the LV stimulation site (such as detected as the first dominant peak on the LV electrogram). The Q-LV interval can be correlated with maximum rate of increase in LV pressure (LV dP/dt max), thus indicative of LV contractility. In another example, S1 intensity can be correlated with LV dP/dt max, thus indicative of the LV contractility. The mechanical delay can include left-ventricular ejection time (LVET), an interval from the opening to the closing of the aortic valve (mechanical systole). The LVET can be correlated with hemodynamic of the LV, and can be measured as an interval between S1 and S2 heart sound within the same cardiac cycle. S1 intensity and LVET therefore can both be used to assess efficacy of the LV electrostimulation therapy delivered using a specified pacing vector. Other examples of the signal metrics can include electromechanical coupling computed using a cardiac electrical signal and a cardiac mechanical signal, such as a cardiac timing interval (CTI). Examples of the CTI can include a pre-ejection period (PEP), a systolic timing interval (STI), or a diastolic timing interval (DTI), among others.

The sensor dynamic response analyzer circuit 231 can use the two or more signal metrics to generate dynamic response indicators for the two or more signal metrics. The dynamic response indicators, which indicate responsiveness of the corresponding signal metric to the stimulation, can be calculated as a rate of change of signal metric values during or after the stimulation. In an example of determining a desired AVD that controls the timing of cardiac resynchronization therapy (CRT), the signal sensor circuit 210 can receive a heart sound (HS) signal during or after the CRT programmed with a specified candidate AVD value. The signal sensor circuit 210 can detect an S1 heart sound during or after the CRT, generate a signal metric of S1 intensity ($\|S1\|$), and trend the $\|S1\|$ over time to produce a temporal response of $\|S1\|$. The sensor dynamic response analyzer circuit 231 can extract from the temporal response the $\|S1\|$ values at two different time instants t1 and t2 ($\|S1\|_{t1}$ and $\|S1\|_{t2}$, respectively), and calculate a dynamic response indicator (DRI) as a rate of change of $\|S1\|$, such as $DRI=(\|S\|_{t1}-\|S1\|_{t2})/(t1-t2)$. A larger DRI value may indicate higher responsiveness of the signal metric $\|S1\|$ to the stimulation, while a smaller DRI value indicating lower responsiveness of $\|S1\|$ to the stimulation. The DRI can alternatively have a categorical value of responsiveness, which can be obtained by comparing the numerical DRI value to one or more thresholds to classify the DRI into one of two or more categories.

The weight factor generation circuit 232 can be coupled to the sensor dynamic response analyzer circuit 231, and produce respective weight factors for the two or more signal metrics using the respective DRI values. The weight factors can be proportional to the respective DRI values. Therefore, if a first $DRI_1$ corresponding to a first signal metric $X_1$ is greater than a second $DRI_2$ corresponding to a second signal metric $X_2$, then a first weight factor $w_1$ corresponding to $X_1$ is greater than a second weight factor $w_2$ corresponding to $X_2$. In an example, the weight factor generation circuit 222 can be configured as a signal metric selector that can select one or more signal metrics by assigning a non-zero weight factor and deselect other one or more metrics by assigning a weight factor equal to zero. A signal metric is deselected (or equivalently having a corresponding weight factor equal to zero) if the corresponding DRI meets a specified condition, such as falls below a threshold DRI value. In some examples, the weight factor generation circuit 232 can produce the weight factors using empirical knowledge about the dynamic responses of the sensors or the signal metrics in addition to or in lieu of the DRI. The empirical knowledge can include historical performance of the signal metrics acquired from the patient or from patient population. In some examples, the weight factor generation circuit 232 can receive user input, such as via the user interface unit 260, to confirm, override, modify, or otherwise manually input weight factors for the signal metrics. Examples of the weight generator circuit 232 are discussed below, such as with reference to FIGS. 4-5.

The stimulation parameter assessment circuit 233 can include a blending circuit 234 and a comparator circuit 235. The blending circuit 234 can generate a stimulation efficacy indicator using a combination of the two or more signal metrics. The stimulation efficacy indicator can indicate a degree of alleviation of an adverse cardiac condition, such as slowing or reversal of worsening HF, a short-term or long-term hemodynamic recovery, an enhancement of cardiac function, or an improvement in patient symptoms or HF comorbidities, among others. In an example, each signal metric can be assigned a score indicative or correlative of a degree of change, or rate of change, of the signal metric resulted from the stimulation (e.g., CRT). A positive score can indicate an improvement of the patient hemodynamic status and a negative score can indicate a deterioration of the patient hemodynamic status. The blending circuit 234 can generate the stimulation efficacy indicator as a numerical composite score using a linear combination of at least some of the two or more signal metrics each weighted by a respective weight factor. The combination can alternatively be a nonlinear combination of the two or more signal metrics such as using a decision tree, a neural network, a fuzzy-logic model, or a multivariate regression model, among others.

The present inventors have recognized that different physiologic sensors, or sensor signal metrics, may respond differently to the stimulation. For example, some sensors or signal metrics indicating cardiac electrical activities can have a faster dynamic response rate (i.e., shorter response time), while some other sensors or signal metrics indicating cardiac mechanical activities can have a slower dynamic response rate (i.e., longer response time) during or after cardiac stimulation. A sensor or signal metric's reliability for estimating the patient hemodynamic status may also be time-dependent. For example, some sensors or signal metrics may be less reliable for detecting short-term patient hemodynamic status but more reliable for detecting long-term patient hemodynamic status. Additionally, patient disease state or health condition may also affect the sensor or signal metric's response to stimulation. For example, for a patient having electrical dyssynchrony between the RV and LV, a sensor or signal metric indicative or correlative of cardiac electrical activation (e.g., QRS width, LV-RV latency) may be more suitable for assessing the effect of stimulation parameter on alleviation of electrical dyssynchrony, whilst for a patient having mechanical dyssynchrony between the RV and LV, a sensor or signal metric indicative or correlative of cardiac mechanical activation (e.g., heart sounds, or cardiac or thoracic impedance) may be more suitable for assessing effect of stimulation parameter on alleviation of mechanical dyssynchrony. The blending circuit 234, by using sensor-specific or signal metric-specific weighting factors that are produced by the weight factor generator circuit 232, can selectively emphasize contributions of some signal metrics, and deemphasize contributions of some other signal metrics to the stimulation efficacy indicator. The resultant stimulation efficacy indicator can be sensitive to, and reliable in detecting, patient hemodynamic status change caused by the stimulation according to the stimulation parameter.

The comparator circuit 235 can assess the adjusted parameter value, and determine the parameter value for the at least one device parameter if the stimulation efficacy indicator meets a specified criterion. In an example where the stimulation efficacy indicator is represented by a numerical composite score, the parameter value can be determined if the composite score exceeds a specified threshold.

The stimulation generator circuit 240 can be configured to generate stimulations for stimulating a target site using electrical, magnetic, or other forms of energy. In an example, the stimulation generator circuit 240 can generate cardiac electrical stimulation according to at least one stimulation parameter, for stimulating one or more cardiac sites including LV, RV, LA, RA, a pulmonary artery, a septum between the left and right ventricles, or other epicardial or endocardial sites. The cardiac electrical stimulation can include CRT of a first site of the LV and a second site of the RV of the heart, according to one or more stimulation parameters such as an AVD, a VVD, or a LRL. Another example of the cardiac electrical stimulation can include multisite stimulation, such as multisite LV pacing, according to one or more of an AVD, intervals between the stimulations at multiple LV sites, among other stimulation parameters. The multisite LV pacing can be achieved using two or more LV pacing vectors. For each LV pacing vector, at least one of the anode or the cathode can be selected from the two or more electrodes on the LV lead 133 (such as electrodes 161 and 162). In an example, the electrostimulation circuit 210 can deliver multisite LV pacing using one or more of a bipolar pacing between two LV electrodes, a bipolar pacing between an LV electrode and a RV or RA electrode, or a unipolar pacing between an LV electrode and the IMD can 112.

In some examples, the stimulation programmer circuit 230 can be configured to adjust the stimulation parameter used in an existing stimulation session when a specified condition is satisfied. In an example, upon the detection of a triggering event such as an event indicative of worsening cardiac condition, the stimulation programmer circuit 230 can adjust parameter value of at least one stimulation parameter such as the AVD, the VVD, or the LRL, and program the stimulation generator circuit 240 to deliver stimulation using the adjusted at least one stimulation parameter. The stimulation programmer circuit 230 can determine an effectiveness of the adjustment or whether further adjustment of the at least one stimulation parameter is needed. The determination can be based on the information about temporal responses of the two or more signal metrics, such as the dynamic response indicators of the two or more signal metrics generated by the sensor dynamic response analyzer circuit 231, as previously discussed with reference to FIG. 2. The blending circuit 234 can determine a stimulation efficacy indicator, which can be computed as a weighted combination of the two or more signal metrics. An adjustment of the parameter value is deemed necessary if the comparator circuit 235 determines such an adjustment (e.g., as an increase or decrease of the stimulation parameter by a specified amount) can result in the stimulation efficacy indicator meeting a specified criterion, such as exceeding a specified threshold. The determined adjustment can then be applied to the stimulation parameter, and the stimulation generator circuit 240 can deliver stimulation according to the adjusted value of the stimulation parameter.

The controller circuit 250 can receive external programming input from the user interface unit 260 to control the operations of the signal sensor circuit 210, the cardiac condition detector circuit 220, the stimulation programmer circuit 230, the stimulation generator circuit 240, and the data flow and instructions between these circuits and respective subcircuits. The controller circuit 250 can configure the cardiac condition detector circuit 220 to detect the triggering event such as an event of worsening HF or other cardiac condition, to configure the stimulation programmer circuit 230 to program the stimulation generator circuit 240 with an adjusted parameter value for at least one stimulation parameter, and to configure the stimulation generator circuit 240 to deliver the stimulation. The controller circuit 250 can configured the signal sensor circuit 210 to sense the physiological signals during and after the stimulation, and to configure the stimulation programmer circuit 230 to produce corresponding weight factors for the two or more signal metrics and determine a parameter value for the stimulation parameter. The controller circuit 250 can configure the stimulation generator circuit 240 to generate the stimulation according to the stimulation parameter with the determined parameter value, and deliver the stimulation to the target tissue.

The user interface unit 260 can include an instruction receiver circuit and a display unit. In an example, at least a portion of the user interface unit 260, such as the display unit, can be implemented in the external system 120. The instruction receiver circuit can include an input device that enables a system user to program the parameters used for electrostimulation or for sensing the physiologic signals. The display unit can display the stimulation parameter with adjustable parameter values, or the trend of the signal metrics before, during, and after the stimulation. The display unit can also display the determined parameter value for the stimulation parameter.

Figure 3:
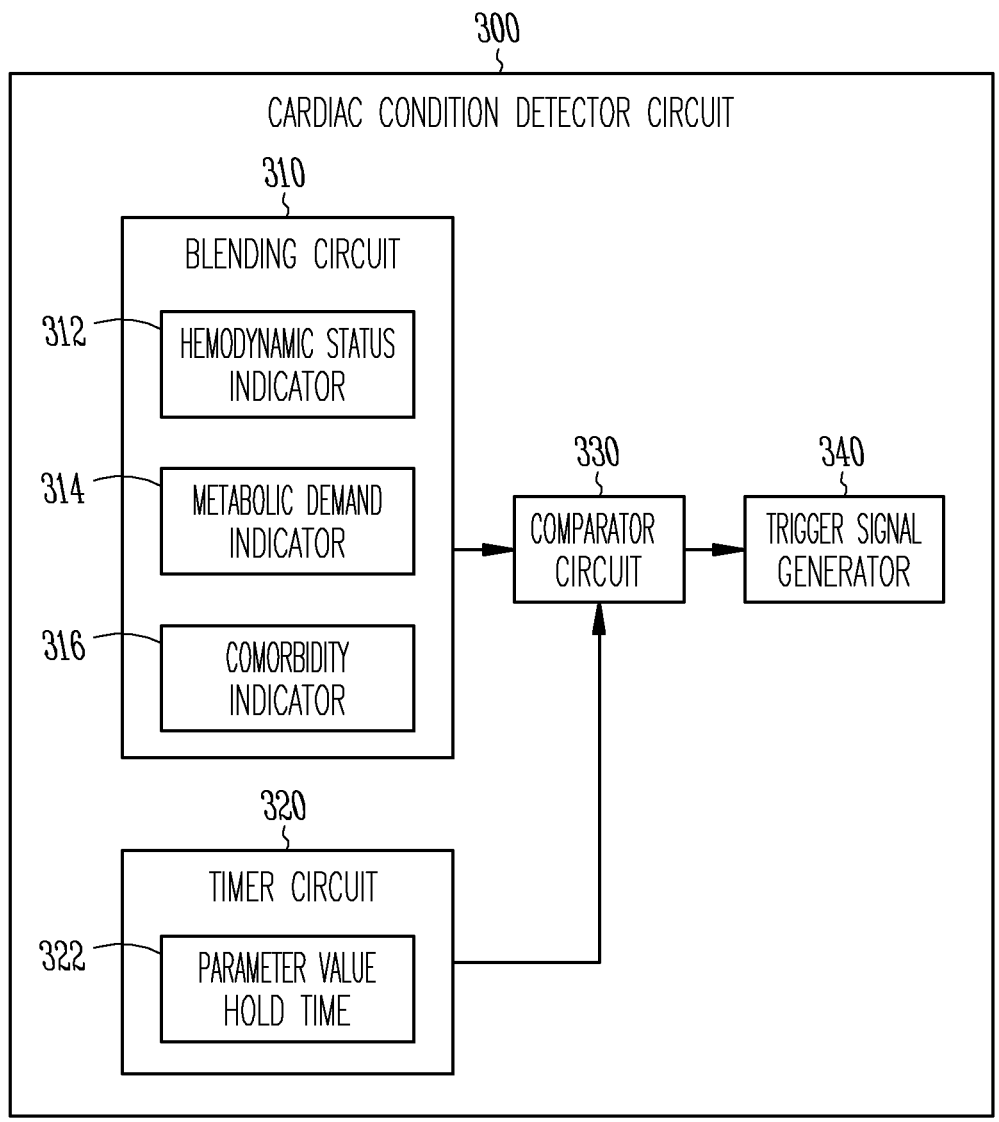
FIG. 3 illustrates generally an example of a cardiac condition detector circuit.

FIG. 3 illustrates generally an example of the cardiac condition detector circuit 300, which can be an embodiment of the cardiac condition detector circuit 220 as illustrated in FIG. 2. The cardiac condition detector circuit 300 can be configured to detect an event indicative of worsening cardiac condition. The detection can trigger the stimulation programmer circuit 230 to adjust the parameter value and determine a value for the stimulation parameter.

The cardiac condition detector circuit 300 can include one or more of a blending circuit 310, a timer circuit 320, a comparator circuit 330, and a trigger signal generator 340. The blending circuit 310 can use two or more signal metrics, such as produced from the one or more physiological signals sensed by the signal sensor signal 210, to generate a cardiac condition indicator such as indicative of worsening HF status in the patient. By way of non-limiting examples, and as illustrated in FIG. 3, the cardiac condition indicator can include one or any combination of a hemodynamic status indicator 312, a metabolic demand indicator 314, or a comorbidity indicator 316. The hemodynamic status indicator 312 indicates a change or a rate of change of hemodynamic status of the patient, and can be computed using signal metrics derived from a heart sound signal, an impedance signal, a blood pressure signal, or a cardiac timing interval signal. Examples of signal metrics indicative or correlative of hemodynamic status can include arterial pressure, pulmonary artery pressure, left atrial pressure, RV pressure, LV coronary pressure, thoracic impedance or cardiac impedance, blood temperature, heart sounds, blood oxygen saturation, or central venous pH value, pre-ejection period (PEP), a systolic timing interval (STI), a diastolic timing interval (DTI), a left ventricular ejection time (LVET), or composite measures such as PEP/LVET ratio, STI/DTI ratio, STI/CL ratio, or DTI/CL ratio, among others.

The metabolic demand indicator 314 indicate a change of metabolic demand in the patient, and can be detected suing signal metrics derived from one or more of a heart rate signal, a respiration signal, a posture signal, a time signal, a body temperature signal, a perspiration signal, or a physical activity signal. A change of metabolic demand, such as an increased or decreased physical activity level, heart rate, respiration rate or depth of the respiration, or body temperature, may require adjustment of stimulation parameter such that the electrical stimulation can offer adequate cardiac output and desirable hemodynamic outcome in adaption to the change in the patient's metabolic demand.

The comorbidity indicator 316 can indicate patient development of comorbidity in HF. A development of a new comorbidity, or worsening of an existing comorbidity, may indicate deteriorating HF status which may require adjustment of stimulation parameter that controls the delivery of therapeutic stimulation. The blending circuit can receive information about presence or severity of one or more HF comorbidities, including hypertension, atrial fibrillation, diabetes mellitus, pneumonia, or renal failure, among other comorbidities. The comorbidity information can be provided by a system user such as via the user interface unit 260, or at least partially automatically retrieved by the cardiac condition detector circuit 300 from a memory circuit that stores up-to-date information about patient's comorbidities in HF.

The timer circuit 320 can determine a parameter value hold time 322 representing time elapsed during which the stimulation parameter is set and maintained at a specified value. When a stimulation parameter has not been updated for an extended period of time (e.g., exceeding a threshold for the parameter value hold time), a trigger signal can be produced by the trigger signal generator 340 to initiate the process of adjustment and optimization of the stimulation parameter. Such periodic triggering of stimulation parameter adjustment can be dependent upon the type of stimulation parameter. In an example, the stimulation parameters may be updated every 1-60 minutes. In another example, the stimulation parameters may be updated every 1-30 days. In another example, the stimulation parameters may be updated every 3-12 months.

The comparator circuit 330 can use one or more of the hemodynamic status indicator 312, the metabolic demand indicator 314, the comorbidity indicator 316, or the parameter value hold time 322 to determine if a criterion for worsening cardiac condition has been met. In an example, an event of worsening cardiac condition is detected when the hemodynamic status indicator 312 or the metabolic demand indicator 314 falls outside a respectively specified range, or when the comorbidity indicator 316 indicates a development of a comorbidity in HF. Upon detection of the event of worsening cardiac condition, the trigger signal generator 340 can generate a signal to trigger the stimulation programmer circuit 230 to initiate the process of determining a value for the stimulation parameter.

In another example, the comparator circuit 330 can compare the parameter value hold time 322 to a specified threshold time. If the parameter value hold time 322 exceeds the threshold time, the trigger signal generator 340 can generate the signal to trigger the stimulation programmer circuit 230 to determine a value for the stimulation parameter. The comparator circuit 330 can alternatively determine both the conditions of whether an event of worsening cardiac condition is detected and whether the parameter value hold time 322 exceeds the specified threshold. The trigger signal generator 340 can generate the trigger signal in response to a detection of worsening cardiac condition and the parameter value hold time 322 exceeding the threshold.

In some examples, the timer circuit 320 can determine time elapsed since a detection of an event of worsening cardiac condition (e.g., an event of worsening HF) using one or more of the hemodynamic status indicator 312, the metabolic demand indicator 314, or the comorbidity indicator 316. The trigger signal generator 340 can generate the trigger signal to trigger the process of determining the parameter value when the time elapsed since the detection of worsening cardiac condition exceeds a specified duration threshold. By confirming that the detected worsening cardiac condition sustains for at least a specified duration before initiating the stimulation parameter adjustment process, an event of worsening cardiac condition can be more reliably detected, thus avoiding stimulation parameter adjustment in response to a false positive detection of worsening cardiac condition.

Figure 4:
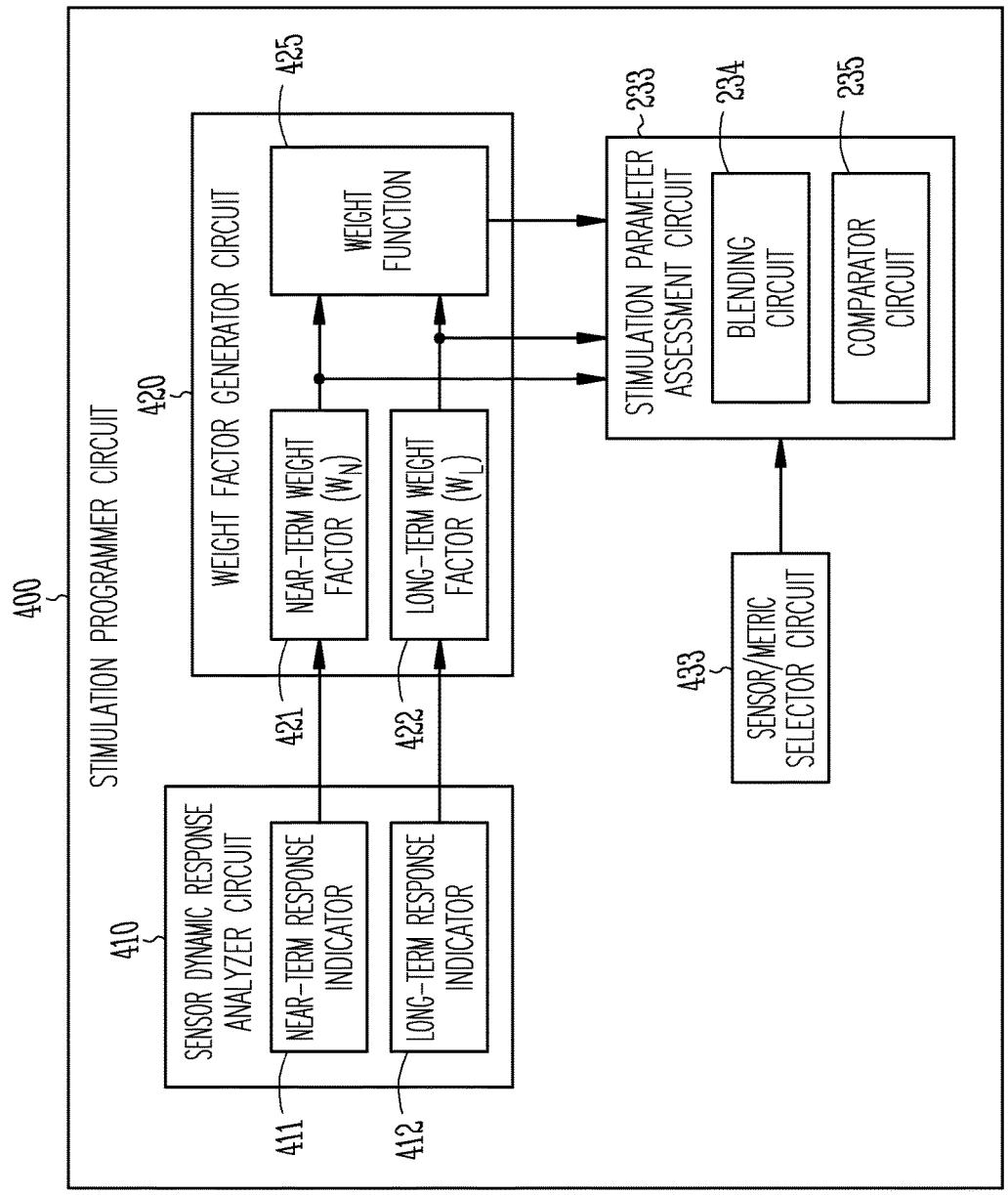
FIG. 4 illustrates generally an example of stimulation programmer circuit.

FIG. 4 illustrates generally an example of stimulation programmer circuit 400, which can be an embodiment of the stimulation programmer circuit 230. The stimulation programmer circuit 400 can include a sensor dynamic response analyzer circuit 410 and a weight factor generator circuit 420, which can be embodiments of the respective subcircuits of the sensor dynamic response analyzer circuit 231 and the weight factor generator circuit 232 as illustrated in FIG. 2.

The sensor dynamic response analyzer circuit 410 can be configured to determine, for each of the two or more signal metrics, a near-term response indicator 411 and a long-term response indicator 412. The near-term response indicator 411 can indicate a change or a rate of change of the corresponding signal metric during a near-term period ($T_N$) during or after the stimulation according to the stimulation parameter with an adjusted parameter value, such as a candidate AVD, VVD, or LRL value. In an example, the near-term period ($T_N$) can be approximately 1-60 minutes following the stimulation. In another example, the near-term period ($T_N$) can be approximately 1-7 days following the stimulation. The long-term response indicator 412 can indicate a change or a rate of change of the corresponding signal metric during a long-term period ($T_L$) following the stimulation according to the stimulation parameter with an adjusted parameter value. In an example, the long-term period $T_L$ can be approximately 20-90 days following the stimulation.

The weight factor generator circuit 420 can produce, for the two or more signal metrics, respective weight factors including one or more of near-term weight factors ($W_N$) 421 for the near-term response indicator during the near-term period $T_N$, or long-term weight factors ($W_L$) 422 for the long-term response indicator during the long-term period $T_L$. The weight factors can be determined based on the dynamic response indicators of corresponding signal metrics. In evaluating the near-term stimulation efficacy (e.g., the near-term hemodynamic recovery resulted from the stimulation), the signal metrics having faster dynamic responses can be emphasized with corresponding larger weight factors, and those having slower dynamic responses can be deemphasized with corresponding smaller weight factors. Likewise, in evaluating the long-term stimulation efficacy, the signal metrics having a more reliable long-term response can be emphasized with a corresponding larger weight factor, and those having a less reliable long-term response can be deemphasized with a corresponding smaller weight factor.

As previously discussed, sensors or signal metrics may have different dynamic responses to stimulation, and different reliability at different time during and after stimulation. The blending circuit 234 can use one or more near-term weight factors ($W_N$) 421 to produce a near-term stimulation efficacy indicator, such as using a combination of at least some of the two or more signal metrics each weighted by the respective near-term weight factors $W_N$. Similarly, the blending circuit 234 can use one or more long-term weight factors ($W_L$) 452 to produce a long-term stimulation efficacy indicator, such as using a combination of at least some of the two or more signal metrics each weighted by the respective long-term weight factors $W_L$.

The weight factor generator circuit 420 can additionally produce, for each of the two or more signal metrics, a respective weight function 425 that describes weight factor as a continuous function of time (hereinafter denoted by "W(t)"), including the near-term period $T_N$ and the long-term period $T_L$ during or after the stimulation. The weight function W(t) can take a value of $W_N$ at a time instant $t_N$ during the short-term period $T_N$, that is, $W_N = W(t_N)$; and take a value of $W_L$ at a time instant $t_L$ during the long-term period $T_L$, that is, $W_L = W(t_L)$. The weight factor thus determined not only depends on the characteristic (e.g., the dynamic response) of the corresponding sensor or signal metric, but also varies with time. The weight function 425 can be a decay function of time if the corresponding signal metric is more responsive to stimulation during the near-term period than during the long-term period. The weight function can be a growth function of time if the corresponding signal metric is less responsive to stimulation during the near-term period than during the long-term period. Examples of the decay or growth function can include one of an exponential function, a logistic function, a logarithm function, a linear function, or a piece-wise linear function, among others. Examples of the weight function 425 are discussed below, such as with reference to FIG. 5.

In additional to or in lieu of the sensor dynamic response indicators (DRI) such as the near-term indicator 411 and the long-term response indicator 412, empirical knowledge about the dynamic responses of the sensors or the signal metrics can be used in determining the weight factors for the signal metrics, or selecting a subset of the two or more signal metrics for use in generating the stimulation efficacy indicator by the blending circuit 234. As illustrated in FIG. 4, the stimulation programmer circuit 400 can include a sensor/metric selector circuit 433 that can be configured to receive information about selection or deselection among the two or more signal metrics according to the stimulation parameter. In an example, the sensor/metric selector circuit 433 can be coupled to the user interface 280 to receive user's input on selection or deselection of one or more signal metrics. In an example, the sensor/metric selector circuit 433 can be coupled to a memory circuit that stores empirical knowledge about the dynamic responses of the sensors or the signal metrics, such as historical performance data of the signal metrics (e.g., dynamic response, or reliability during the long-term period), acquired from the patient, or from patient population. The information stored in the memory circuit can include a look-up table or an association map establishing a correspondence between selectable signal metrics and the stimulation parameters. The sensor/metric selector circuit 433 can select one or more of: S1 amplitude or heart rate if the stimulation parameter is atrio-ventricular delay (AVD); Q-LV interval if the stimulation parameter is RV-LV delay (VVD); a blood pressure metric if the stimulation parameter is lower rate limit LRL; or one or more of impedance metric or physical activity metric if the stimulation parameter is capture threshold. The blending circuit 234 can generate the stimulation efficacy indicator using a combination of the selected signal metrics weighted by the respective weight factors, such as those produced by the weight factor generator circuit 420.

Figure 5:
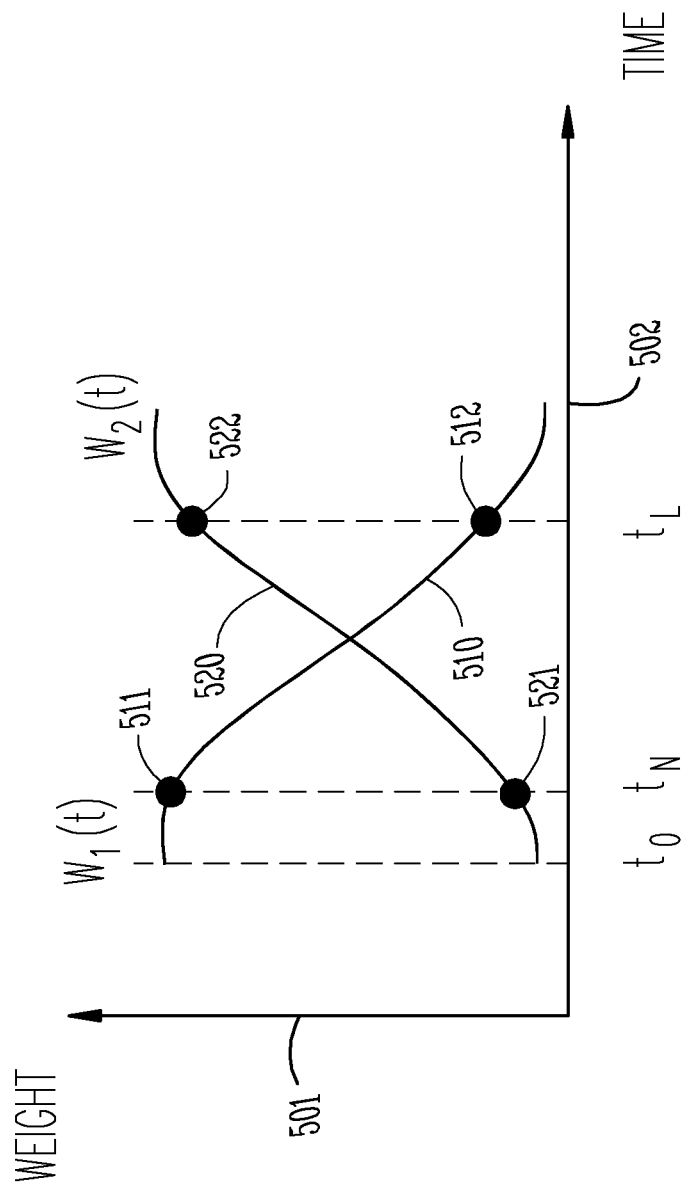
FIG. 5 illustrates generally an example of the time-dependent weight function.
Figure 6:
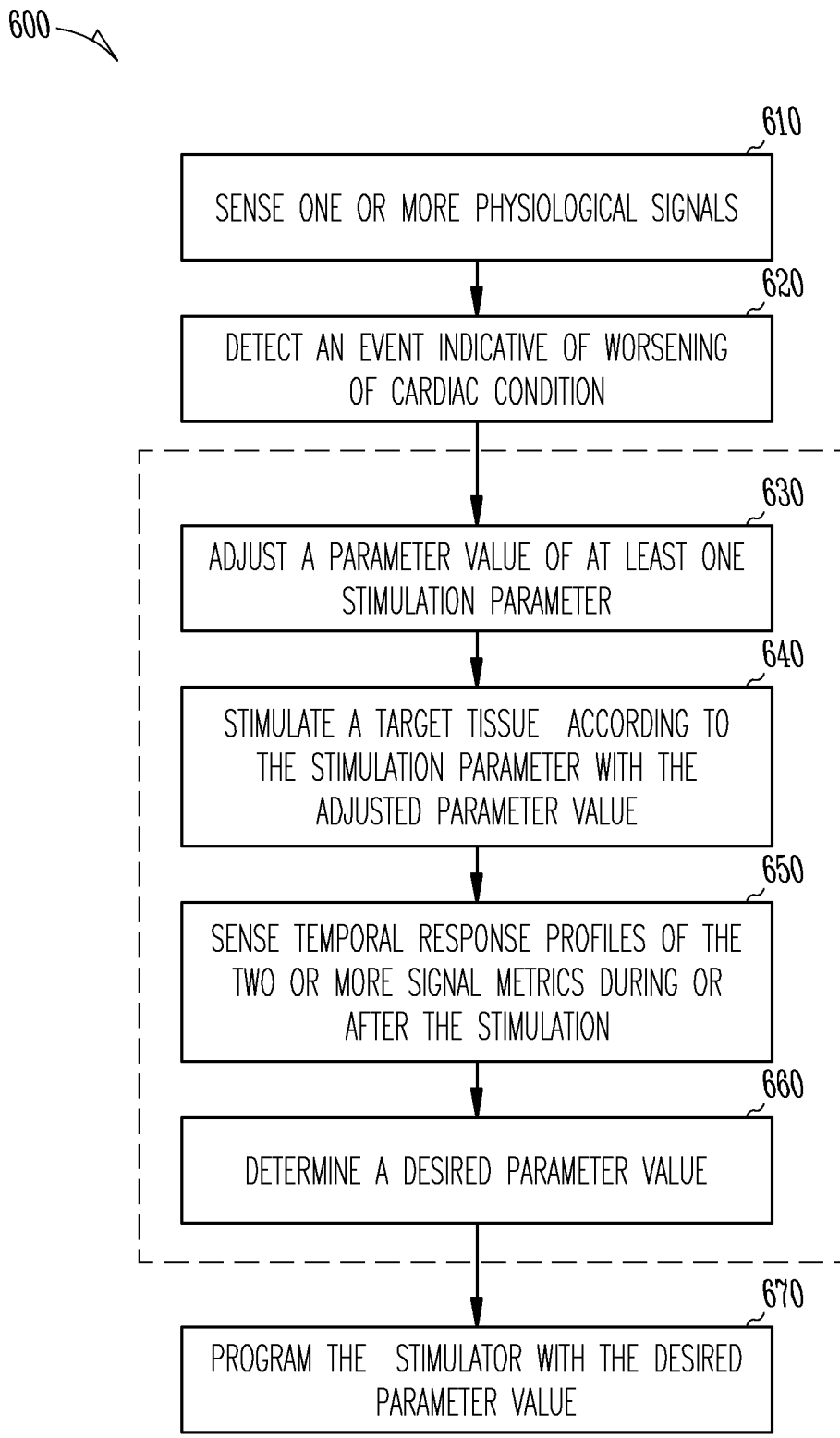
FIG. 6 illustrates generally an example of a method for determining a device parameter and stimulating a target site according to the determined device parameter.

FIG. 5 illustrates generally an example of the time-dependent weight function 460, which describes values of the weight factor shown in the y-axis 501 as a continuous function of time shown in the x-axis 502. The weight functions $W_1(t)$ and $W_2(t)$ can have respective temporal patterns that are in accordance with the temporal responses of the respective signal metrics (e.g., responses during the near-term and long-term periods). By way of example and not limitation, a first weight function $W_1(t)$ corresponds to a signal metric that is more responsive to stimulation during the near-term period, such as a QRS width, Q-LV interval, RV-LV intervals, or other electrical signal metrics. Accordingly, the first weight function W 40 is a decay function 510 of time. Also by way of example and not limitation, a second weight function $W_2(t)$ can correspond to a signal metric that is more reliable during the long-term period than during the near-term period, such as a S1 or S3 heart sound intensity, thoracic or cardiac impedance, physical activities, or other mechanical signal metrics. Accordingly, the second weight function $W_2(t)$ is a growth function 520 of time. Following an initiation of stimulation at time to, at the beginning ($t_N$) of the near-term period $T_N$, $W_1(t)$ has a value 511 greater than a value 521 of $w_2(t)$, that is, $W_1(t_N) > W_2(t_N)$. Following the stimulation, the weight functions $W_1(t)$ decreases and $W_2(t)$ increases as time elapses. When the sensor responses reach the post stimulation steady state at $t_L$ that marks the long-term period $T_L$, $W_1(t)$ has a value 512 smaller than a value 522 of $W_2(t)$, that is, $W_1(t_L) < W_2(t_L)$. The different temporal patterns of weight functions $W_1(t)$ and $W_2(t)$ during and after the stimulation can allow the blending circuit 234 to produce the stimulation efficacy indicator (e.g., a combination of signal metrics) that emphasizes of the contribution of the signal metrics with faster dynamic response during the near-term period, while emphasizing the contribution of the signal metrics with a more reliable long-term response during the long-term period FIG. 6 illustrates generally an example of a method 600 for determining a device parameter and stimulating a target site according to the determined device parameter, such as a stimulation parameter associated with timing of stimulation. In an example, the IMD 110, including its various examples discussed in this document, can be programmed to perform method 500, including its various examples discussed in this document.

In an example, the method 600 can be used to determine a value for a stimulation parameter that controls the timing of delivery of cardiac resynchronization therapy (CRT) or multisite cardiac stimulation such as multisite left-ventricular (LV) pacing. The stimulation parameter can include a relative timing between a first event in a first site of the heart and a second event in a second site of the heart, such as an atrial-ventricular delay (AVD), a left ventricular-right ventricular delay (VVD). The AVD represents a latency between an intrinsically occurred atrial electrical activation signal (As) and a subsequent ventricular pacing pulse (Vp), or between an atrial pacing pulse (Ap) and the subsequent Vp. The VVD represents the latency between a left ventricular pacing pulse (LVp) and the subsequent right ventricular pacing pulse (RVp). The stimulation parameter can include a lower rate limit (LRL) which indicates a lowest rate that a cardiac stimulation may be initiated. The determined values of the one or more stimulation parameters can be programmed to a cardiac stimulator that generate stimulation pulses for stimulating one or more sites in the heart to restore or improve the cardiac function.

One or more physiologic signals can be sensed at 610. Examples of the physiologic signal can include one or more of intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, posture, respiration, body weight, or body temperature. The physiologic signals can be acquired by one or more physiologic sensors including, for example, pressure sensors, flow sensors, impedance sensors, accelerometers, microphone sensors, respiration sensors, temperature sensors, and blood chemical sensors. The physiologic sensors can be implanted inside a patient's body or external to the patient. From the physiologic signals, two or more signal metrics can be generated. In an example, the physiologic signal can include a transthoracic impedance signal sensed via the electrodes on one or more of the implantable leads such as 108A-C and the can 112, and a signal metric of direct-current (DC) impedance can be generated using the transthoracic impedance signal. In another example, the physiologic signal can include a heart sound (HS) signal, and the HS metrics can include S1 intensity, S2 intensity, S3 intensity, or timing metrics of the S1, S2, or S3 heart sound with respect to a fiducial point such as a P wave or R wave on an ECG or an EGM.

At 620, a cardiac condition indicator can be generated using the two or more signal metrics, and an event indicative of worsening cardiac conditions, such as worsening heart failure (HF), can be detected when the cardiac condition meets a specified condition, such as falling within a specified range. In an example, the cardiac condition indicator can include one or a combination of a change or a rate of change of one or more signal metrics obtained from the sensed physiological signals. Examples of generating the cardiac condition indicator are discussed below, such as with reference to FIG. 7.

In response to the detection of the event of worsening cardiac condition, a process of determine a value for the stimulation parameter can be initiated. The process includes one or more of steps 630-660. At 630, a stimulator, such as the stimulation generator circuit 240 or any variant thereof, can be configured by programming the stimulator with a candidate parameter value for at least one stimulation parameter, such as candidate values of one or more of AVD, the VVD, or the LRL. The stimulator can generate electrical stimulation according to the stimulation parameter with the adjusted parameter value to stimulate the target tissue at 640.

During or after the electrical stimulation, at 650 one or more physiological signals can be sensed, and temporal responses of the two or more signal metrics can be generated. Examples of the signal metrics can include: intensities (such as amplitudes) and timing of P wave, Q wave, R wave, QRS complex, or T wave on a ECG; timing of sensed activation of at least a portion of a chamber of the heart such as RA, RV, and LV, obtained from the intracardiac EGMs; electrical delay of a chamber of the heart such as LV electrical delay; interventricular conduction delay measured as the delay between LV activation to RV activation (LV-RV) delay; intraventricular delay; intensity of a component of the sensed HS signal including one or more of S1, S2, S3, or S4 heart sounds; mechanical delay such as time intervals indicative of systole or diastole; pressures inside a heart chamber; end-systolic volume; or end-diastolic volume; among others. The temporal responses can include near-term and long-term responses to the stimulation, and can be predictive of patient hemodynamic response to the therapeutic cardiac electrostimulation.

At 660, a value for the stimulation parameter can be determined based on the information about temporal responses of the signal metrics. In an example, a stimulation efficacy indicator can be produced using a combination of the two or more signal metrics. The stimulation efficacy indicator can indicate the degree of alleviation of an adverse cardiac condition, such as a slowing or reversal of worsening HF, a short-term or long-term hemodynamic recovery, an enhancement of cardiac function, or an improvement in patient symptoms or HF comorbidities. The parameter value for the device parameter can then be determined if the stimulation efficacy indicator meets a specified criterion. In some examples, a determination of adjustment of the parameter value used in an existing stimulation session can be made at 660. The determination can include an effectiveness of an adjustment or whether further adjustment of a stimulation parameter is needed, based on the information about temporal responses of the signal metrics. Examples of generating the stimulation efficacy indicator and determining the parameter value are discussed below, such as with reference to FIG. 8.

At 670, the parameter value can be programmed into the stimulator, which can generate stimulation for stimulating a target site. The stimulation can include cardiac stimulation according to at least one stimulation parameter to stimulate one or more sites of LV, LA, RV, or RA, a pulmonary artery, a septum between the left and right ventricles, or other epicardial or endocardial sites. The cardiac stimulation can include cardiac resynchronization therapy (CRT) of a first site of the LV and a second site of the RV of the heart. The cardiac stimulation can include multisite stimulation, such as multisite LV pacing of at least first and second sites at the LV, according to one or more stimulation parameters.

Figure 7:
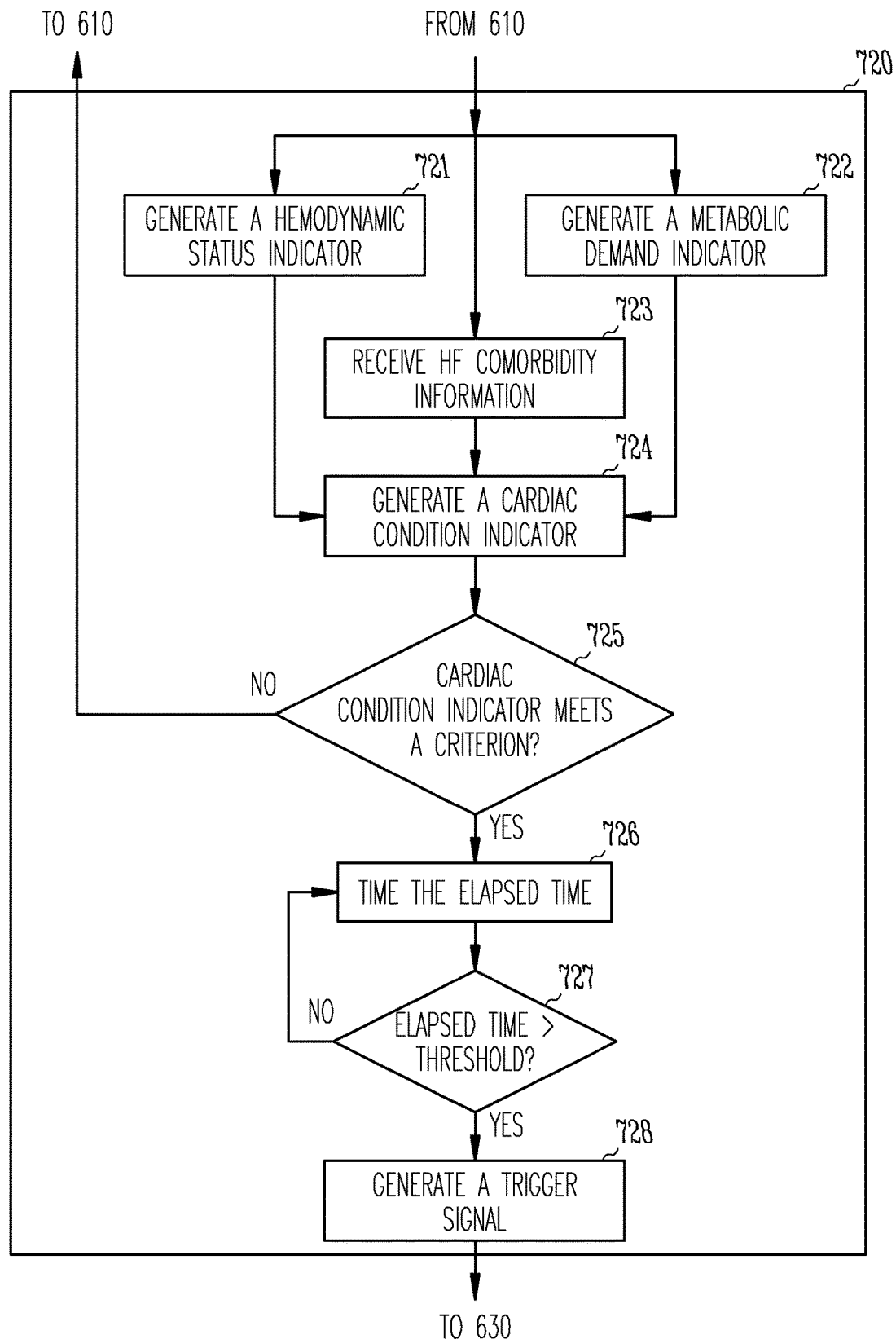
FIG. 7 illustrates generally an example of a method for generating a cardiac condition indicator using the one or more physiological signals.

FIG. 7 illustrates generally an example of a method 720 for generating a cardiac condition indicator, such as an indicator of worsening HF, using the one or more physiological signals received at 610. The method 720 can be an embodiment of the step 620 in FIG. 6. The cardiac condition detector circuit 300, including its various examples discussed in this document, can be programmed to perform method 720, including its various examples discussed in this document.

The method 720 can include a process of generating one or more of a hemodynamic status indicator at 721, or a metabolic demand indicator at 722, or receiving HF comorbidity information at 723. The hemodynamic status indicator can indicate a change or a rate of change of hemodynamic status of the patient, which can be computed using two or more signal metrics indicative or correlative of hemodynamic status. Examples of signal metrics can include arterial pressure, pulmonary artery pressure, left atrial pressure, RV pressure, LV coronary pressure, thoracic impedance or cardiac impedance, blood temperature, heart sounds, blood oxygen saturation, or central venous pH value, pre-ejection period (PEP), a systolic timing interval (STI), a diastolic timing interval (DTI), a left ventricular ejection time (LVET), or composite measures such as PEP/LVET ratio, STI/DTI ratio, STI/CL ratio, or DTI/CL ratio, among others. The metabolic demand indicator produced at 722 can indicate a change of metabolic demand in the patient, which can be computed using one or more of a heart rate signal, a respiration signal, a posture signal, a time signal, a temperature signal, a perspiration signal, or a physical activity signal. The information about development of comorbidity in HF received at 723 can indicate presence or severity of one or more of hypertension, atrial fibrillation, diabetes mellitus, pneumonia, or renal failure, among other comorbidities.

At 724, a cardiac condition indicator can be generated using one or more of the hemodynamic status indicator, the metabolic demand indicator, or the comorbidity information. The cardiac condition indicator can be compared to specified criterion at 725 to determine occurrence of an event of worsening cardiac condition. In an example, an event of worsening cardiac condition is detected when one or more of the hemodynamic status indicator or the metabolic demand indicator falls outside a respectively specified range, or when there is indication of development of a comorbidity in HF. If the cardiac condition indicator fails to meet the criterion at 725, then no event of worsening cardiac condition is detected. The process continues at 610 to receive additional date of the one or more physiological signals. If the cardiac condition indicator meets the criterion at 725, then an event of worsening cardiac condition is deemed detected.

The method 720 can include a step of timing the elapsed time during which the at least one stimulation parameter is set and maintained at a specified parameter value. When a stimulation parameter has not been updated over a specified period of time (hereinafter referred to as parameter value hold time), adjustment of stimulation parameter can be attempted. The periodic triggering of stimulation parameter update at specified duration can be dependent upon the type of stimulation parameter. In an example, a trigger signal can be generated to trigger the process of determining the value for the stimulation parameter when an event of worsening HF is detected and when the parameter value hold time exceeds the threshold time.

In an example, the trigger signal can be generated only when the detected worsening cardiac condition sustains for an extended period. The method 700 can include a step 726 of determining the time elapsed since a detection of an event of worsening cardiac condition (based on one or more of the hemodynamic status indicator, the metabolic demand indicator, or the comorbidity information). When the time elapsed from the detection of the event of worsening cardiac condition exceeds a specified duration threshold at 727, a trigger signal be generated at 728 to trigger the process of determining the value for the stimulation parameter. The confirmation of the detected worsening cardiac condition sustaining for at least a specified duration before initiating the stimulation parameter adjustment can avoid stimulation parameter update in response to a false positive detection of worsening cardiac condition.

Figure 8:
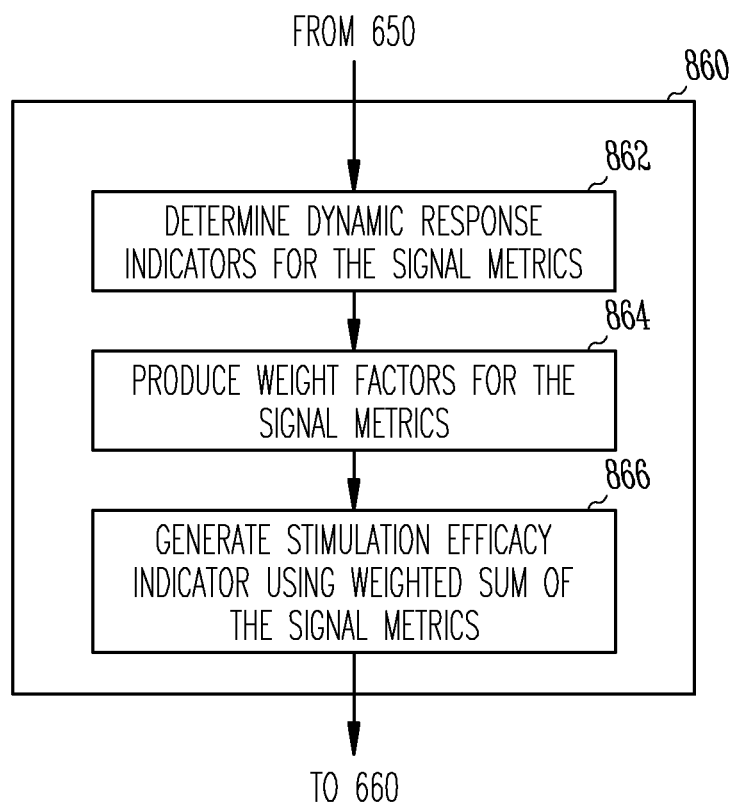
FIG. 8 illustrates generally an example of a method for generating the stimulation efficacy indicator and determining the parameter value.

FIG. 8 illustrates generally an example of a method 860 for generating the stimulation efficacy indicator and determining the parameter value. The method 860 can be an embodiment of the step 660 in FIG. 6 for determining the value for the at least one stimulation parameter, and can be implemented in the stimulation programmer circuit 230, or the stimulation programmer circuit 400.

At 862, the temporal responses of the two or more signal metrics, such as produced at 650, can be used to produce respective dynamic response indicators (DRIs) indicating responsiveness of the two or more signal metrics to the stimulation. The DRI can have a numerical or a categorical value. In an example where the signal metric includes an S1 heart sound intensity ∥S1∥, the DRI can be calculated as a rate of change of S1 intensity at two different time instants $t_1$ and $t_2$ during or after the stimulation according to a specified value of AVD, that is, DRI=(∥S1∥$_{t1}$−∥S1∥$_{t2}$)/(t1−t2). A larger DRI value indicates higher responsiveness of the signal metric ∥S1∥ to the stimulation, while a smaller DRI value indicating lower responsiveness of ∥S1∥ to the stimulation.

At 864, respective weight factors can be produced for the two or more signal metrics using the respective dynamic response indicators. In an example, the weight factor can be proportional to the DRI value. In another example, the weight factor can be used as a signal metric selector, such that one or more signal metrics can be selected by assigning a non-zero weight factor, while other one or more metrics can be deselect by assigning a weight factor equal to zero. A signal metric is deselected if the corresponding DRI meets a specified condition, such as falls below a threshold DRI value. In addition to or in lieu of the DRI, empirical knowledge about the dynamic responses of the sensors or the signal metrics, such as historical performance data of the signal metrics population data can be used to determine the DRI.

At 866, a stimulation efficacy indicator can be generated using a combination of at least some of the two or more signal metrics each weighted by the respective weight factor. The stimulation efficacy indicator can indicate the degree of alleviation an adverse cardiac condition, such as a slowing or reversal of worsening HF, a short-term or long-term hemodynamic recovery, an enhancement of cardiac function, or an improvement in patient symptoms or HF comorbidities. In an example, each signal metric can be assigned a score that is indicative or correlative of a degree of change, or rate of change, of the signal metric resulted from the electrical stimulation. A positive score can indicate an improvement of the patient hemodynamic status and a negative score can indicate a deterioration of the patient hemodynamic status.

In some examples, the dynamic response indicators determined at 862 can include one or more of near-term response indicators during a near-term period ($T_N$) with reference to the stimulation, or one or more long-term response indicators during a long-term period ($T_L$) with reference to the stimulation. The respective weight factors produced at 864 can include respective one or more of near-term weight factors ($W_N$) corresponding to the near-term period or long-term weight factors ($W_L$) corresponding to the long-term period for the two or more signal metrics. The stimulation efficacy indicator generated at 866 can include near-term stimulation efficacy indicator using a combination of at least some of the two or more signal metrics each weighted by the respective near-term weight factors, or a long-term stimulation efficacy indicator using a combination of at least some of the two or more signal metrics each weighted by the respective long-term weight factors. In evaluating the near-term stimulation efficacy, the signal metrics having a faster dynamic response can be emphasized with a corresponding larger weight factor, and those having a slower dynamic response can be deemphasized with a corresponding smaller weight factor. Similarly, in evaluating the long-term stimulation efficacy, the signal metrics having a more reliable long-term response can be emphasized with a corresponding larger weight factor, and those having a less reliable long-term response can be deemphasized with a corresponding smaller weight factor.

In some examples, the weight factors produced at 864 can include producing respective weight functions for the two or more signal metrics. Each weight function can describe weight factor as a respective function of time. The weight factor thus determined is not only dependent on the characteristic (e.g., the dynamic response) of the corresponding sensor or signal metric, but also varies with time. In an example, as illustrated in FIG. 5, the weight function can be a decay function of time if the corresponding signal metric is more responsive to stimulation during the near-term period than during the long-term period. The function can be a growth function of time if the corresponding signal metric is less responsive to stimulation during the near-term period than during the long-term period. The stimulation efficacy indicator can be generated at 866 using a combination of the selected signal metrics weighted by the respective weight factors. The resulting stimulation efficacy indicator can be used at 660 to determine the value of the stimulation parameter.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical-device system, comprising:
   a detector circuit configured to detect a cardiac status of a patient using physiological information of the patient including two or more physiological signal metrics;
   a stimulation programmer circuit configured to determine temporal information indicative of responsiveness of the two or more physiological signal metrics evoked by stimulation of the patient, and to select or update a stimulation site using the determined temporal information; and
   a stimulation generator circuit configured to generate stimulation energy to stimulate target tissue of the patient according to the selected or updated stimulation site.

2. The system of claim 1, wherein the stimulation programmer circuit is configured to determine time intervals for reconfiguring a device parameter based on the detected cardiac status, the reconfiguring the device parameter including selecting or updating the stimulation site.

3. The system of claim 2, wherein the stimulation programmer circuit is configured to determine a reconfiguration frequency based on the detected cardiac status, and to select or update the stimulation site according to the determined reconfiguration frequency.

4. The system of claim 3, wherein the device parameter includes a stimulation timing parameter, and the stimulation programmer circuit is configured to determine or update the stimulation timing parameter according to the determined reconfiguration frequency.

5. The system of claim 3, wherein the stimulation programmer circuit is configured to determine the reconfiguration frequency using a first period of time elapsed during which the device parameter is set and maintained at a specified parameter value, and to select or update the stimulation site in response to the first time period exceeding a specific threshold.

6. The system of claim 3; wherein the stimulation programmer circuit is configured to determine the reconfiguration frequency using a second period of time elapsed since the detection of an event of worsening cardiac condition, and to select or update the stimulation site in response to the second time period exceeding a specific threshold.

7. The system of claim 1, wherein the stimulation programmer circuit is configured to select or update the stimulation site in response to a worsening cardiac condition.

8. The system of claim 1, wherein the stimulation programmer circuit is configured to select the stimulation site, including to select one or a combination of:
   at least one left ventricular (LV) stimulation site; or
   at least one right ventricular (RV) stimulation site.

9. The system of claim 8, wherein the stimulation programmer circuit is configured to select between a cardiac resynchronization therapy (CRT) including pacing at an LV stimulation site and an RV stimulation site, and a multisite pacing (MSP) of two or more stimulation sites of a same heart chamber.

10. The system of claim 9; wherein the stimulation programmer circuit is configured to select the CRT, and to determine or adjust a value of a CRT parameter using the temporal information of the two or more physiological signal metrics, the CRT parameter including one or more of an atrio-ventricular delay, a RV-LV delay, or a lower rate limit for stimulation.

11. The system of claim 9, wherein the stimulation programmer circuit is configured to select the MSP, and to determine or adjust a value of an MSP parameter using the temporal information of the two or more physiological signal metrics, the MSP parameter including one or more of an atrio-ventricular delay, or a time delay between stimulations respectively delivered at two or the two or more stimulation sites.

12. The system of claim 1, wherein the stimulation programmer circuit is configured to select or update the stimulation site further using one or more of:
   hemodynamic status information;
   metabolic demand information; or
   heart failure comorbidity information.

13. A method, comprising:
   detecting, via a detector circuit, a cardiac status of a patient using physiological information of the patient including two or more physiological signal metrics;

determining, via a stimulation programmer circuit, temporal information indicative of responsiveness of the two or more physiological signal metrics evoked by stimulation of the patient;

selecting or updating, via the stimulation programmer circuit, a stimulation site using the determined temporal information; and generating, via a stimulation generator circuit, stimulation energy to stimulate target tissue of the patient according to the selected or updated stimulation site.

14. The method of claim 13, comprising determining a reconfiguration frequency for reconfiguring a device parameter based on the detected cardiac status, wherein reconfiguring the device parameter includes selecting or updating the stimulation site.

15. The method of claim 14, wherein the device parameter includes a stimulation timing parameter, the method comprising determining or updating the stimulation timing parameter according to the determined reconfiguration frequency.

16. The method of claim 14, wherein determining the reconfiguration frequency includes using a first period of time elapsed during which the device parameter is set and maintained at a specified parameter value, and wherein selecting or updating the stimulation site is in response to the first time period exceeding a specified threshold.

17. The method of claim 14, wherein determining the reconfiguration frequency includes using a second period of time elapsed since the detection of an event of worsening cardiac condition, and wherein selecting or updating the stimulation site is in response to the second time period exceeding a specified threshold.

18. The method of claim 13, wherein selecting or updating the stimulation site is in response to a trigger event of worsening cardiac condition.

19. The method of claim 13, wherein selecting or updating the stimulation site includes selecting or updating one or more of:
 at least one left ventricular (LV) stimulation site; or
 at least one right ventricular (RV) stimulation site.

20. The method of claim 13, wherein selecting or updating the stimulation site includes selecting between a cardiac resynchronization therapy including pacing at an LV stimulation site and an RV stimulation site, and a multisite pacing of two or more stimulation sites of a same heart chamber.

* * * * *